US009572582B2

(12) United States Patent
Beane et al.

(10) Patent No.: US 9,572,582 B2
(45) Date of Patent: Feb. 21, 2017

(54) METHOD AND APPARATUS FOR EFFECTING A MINIMALLY INVASIVE DISTAL ANASTOMOSIS FOR AN AORTIC VALVE BYPASS

(71) Applicant: Correx, Inc., Waltham, MA (US)

(72) Inventors: Richard M. Beane, Hingham, MA (US); Ronald Boudreau, Boxborough, MA (US); James Alan Crunkleton, Weston, MA (US); Anthony G. Liepert, Lincoln, MA (US); Joseph L. Smith, Jr., Concord, MA (US)

(73) Assignee: Correx, Inc., Waltham, MA (US)

( * ) Notice: Subject to any disclaimer, the term of this patent is extended or adjusted under 35 U.S.C. 154(b) by 238 days.

(21) Appl. No.: 13/961,556

(22) Filed: Aug. 7, 2013

(65) Prior Publication Data

US 2014/0194909 A1    Jul. 10, 2014

Related U.S. Application Data

(63) Continuation of application No. 12/857,115, filed on Aug. 16, 2010, now abandoned.
(Continued)

(51) Int. Cl.
*A61B 17/11* (2006.01)
*A61B 17/00* (2006.01)

(52) U.S. Cl.
CPC ............ *A61B 17/11* (2013.01); *A61B 17/1114* (2013.01); *A61B 2017/00243* (2013.01);
(Continued)

(58) Field of Classification Search
CPC ................. A61B 17/11; A61B 17/1114; A61B 2017/1107; A61B 2017/1121; A61B 2017/1132; A61B 2017/1135; A61B 2017/1139
See application file for complete search history.

(56) References Cited

U.S. PATENT DOCUMENTS 4,366,819 A * 1/1983 Kaster .................... A61B 17/11
                                                                606/153
6,007,576 A * 12/1999 McClellan ............. A61F 2/064
                                                                623/23.64
(Continued)

FOREIGN PATENT DOCUMENTS

EP        1 599 151      11/2005
EP        2 111 243      10/2009
(Continued)

*Primary Examiner* — Todd J Scherbel
(74) *Attorney, Agent, or Firm* — Pandiscio & Pandiscio

(57) ABSTRACT

A connector for joining a first hollow structure to the side wall of a second hollow structure, the connector comprising a first component comprising an inner collar; a hollow body; and a graft mounted to the inner collar and forming a conduit through the hollow body and the inner collar; and a second component comprising an outer collar and a hollow body, the hollow body of the second component being sized for coaxial disposition over the hollow body of the first component so that the outer collar of the second component can be adjustably positioned relative to the inner collar of the first component and so that the conduit of the graft provides fluid communication between (i) the region beyond the inner collar, and (ii) the region beyond the hollow body of the first component.

12 Claims, 16 Drawing Sheets

Related U.S. Application Data

(60) Provisional application No. 61/234,075, filed on Aug. 14, 2009.

(52) U.S. Cl.
CPC .............. *A61B 2017/1107* (2013.01); *A61B 2017/1121* (2013.01); *A61B 2017/1132* (2013.01); *A61B 2017/1135* (2013.01); *A61B 2017/1139* (2013.01)

(56) References Cited

U.S. PATENT DOCUMENTS

| | | | |
|---|---|---|---|
| 6,165,196 A * | 12/2000 | Stack | A61B 17/11 606/194 |
| 6,241,743 B1 * | 6/2001 | Levin | A61B 17/0643 606/153 |
| 7,077,801 B2 | 7/2006 | Haverich | |
| 7,510,561 B2 | 3/2009 | Beane et al. | |
| 7,766,811 B2 | 8/2010 | Haverich | |
| 8,361,092 B1 * | 1/2013 | Asfora | A61B 17/08 606/153 |
| 2001/0001122 A1 | 5/2001 | Gifford, III et al. | |
| 2003/0225425 A1 | 12/2003 | Kupiecki et al. | |
| 2008/0195125 A1 | 8/2008 | Hoffman | |
| 2010/0114306 A1 | 5/2010 | Lenihan et al. | |

FOREIGN PATENT DOCUMENTS

| | | |
|---|---|---|
| WO | WO 99/17662 | 4/1999 |
| WO | WO 99/63910 | 12/1999 |
| WO | WO 2008/040580 | 4/2008 |

\* cited by examiner

METHOD AND APPARATUS FOR EFFECTING A MINIMALLY INVASIVE DISTAL ANASTOMOSIS FOR AN AORTIC VALVE BYPASS

REFERENCE TO PENDING PRIOR PATENT APPLICATION

This patent application is a continuation of pending prior U.S. patent application Ser. No. 12/857,115, filed Aug. 16, 2010 by Richard M. Beane et al. for METHOD AND APPARATUS FOR EFFECTING A MINIMALLY INVASIVE DISTAL ANASTOMOSIS FOR AN AORTIC VALVE BYPASS, which in turn claims benefit of prior U.S. Provisional Patent Application Ser. No. 61/234,075, filed Aug. 14, 2009 by Richard M. Beane et al. for MINIMALLY INVASIVE DISTAL ANASTOMOSIS FOR AORTIC VALVE BYPASS.

The above-identified patent applications are hereby incorporated herein by reference.

FIELD OF THE INVENTION

This invention relates to surgical methods and apparatus in general, and more particularly to surgical methods and apparatus for effecting an aortic valve bypass.

BACKGROUND OF THE INVENTION

Aortic valve bypass is a proven procedure for relieving critical aortic valve stenosis. This procedure comprises the deployment of a bypass conduit, having a prosthetic valve disposed therein, between the left ventricle and the descending aorta. This approach allows blood to be pumped from the left ventricle into the descending aorta without requiring removal of the dysfunctional native aortic valve. See FIG. 1.

In an aortic valve bypass procedure, the connection of the bypass conduit to the descending aorta is commonly referred to as the "distal anastomosis", and is currently one of the more difficult and time-consuming elements of an aortic valve bypass procedure.

Currently, in order to effect the distal anastomosis, it is necessary to perform an anterior lateral thoracotomy of approximately six inch length in order to gain sufficient access to the descending aorta. The descending aorta is side-clamped so as to engage, but not occlude, the artery. Then a longitudinal slit is made in the clamped portion of the artery wall, and a graft (e.g., the distal end of the bypass conduit, or an element which is to be secured to the distal end of the bypass conduit), typically 14-20 mm in diameter, is sutured in place, substantially perpendicular to the side wall of the descending aorta, so as to establish the desired fluid connection. Once the perimeter of the graft has been secured to the slit aortic wall, the side clamp can be released and the distal anastomosis is complete.

With respect to the foregoing, it should be appreciated that the thickness of the side wall of the descending aorta can vary considerably from patient to patient. Factors influencing the thickness of the side wall of the descending aorta can include, but are not limited to, the presence of exterior fat and connective tissue, interior calcium deposits, and interior ulcerations. In practice, the thickness of the side wall of the descending aorta can vary from about 1 mm to about 4 mm in thickness. This variation in the thickness of the side wall of the descending aorta is a factor which may need to be taken into account when forming the distal anastomosis.

Aortic valve bypass is not currently a common procedure, at least in part due to the relatively difficult and time-consuming nature of the distal anastomosis. Furthermore, aortic valve bypass cannot currently be considered to be a minimally invasive procedure, due to the need to provide an anterior lateral thoracotomy of approximately 6 inch length. However, reducing the size of the thoracotomy with the current procedure is problematic at best, since reduced access to the descending aorta makes cross-clamping and suturing all the more difficult and time-consuming. Also, when the ribs are spread to create access to the thoracic cavity, the ribs can sometimes fracture, thereby causing additional trauma to the patient.

Consequently, there is a need for an improved method and apparatus for effecting the distal anastomosis in an aortic valve bypass procedure.

SUMMARY OF THE INVENTION

These and other objects of the present invention are addressed by the provision and use of a novel method and apparatus for effecting the distal anastomosis in an aortic valve bypass procedure.

In one form of the invention, there is provided a connector for joining a first hollow structure to the side wall of a second hollow structure, the connector comprising:
a first component comprising:
an inner collar for disposition within the interior of the second hollow structure, the inner collar having a toroidal configuration characterized by an outer perimeter and an inner perimeter, with the inner collar being flexible;
a hollow body connected to the inner collar and upstanding therefrom, the hollow body of the inner collar being aligned with the inner perimeter of the inner collar; and
a graft element mounted to the inner collar and forming a conduit extending through the hollow body and the inner perimeter of the inner collar, the graft being formed out of a fluid-retaining material; and
a second component for disposition outside the second hollow structure, the second component comprising an outer collar and a hollow body connected to the outer collar, the outer collar having a toroidal configuration characterized by an outer perimeter and an inner perimeter, with the hollow body of the outer collar being aligned with the inner perimeter of the outer collar;
the hollow body of the second component being sized for coaxial disposition over the hollow body of the first component so that the outer collar of the second component can be adjustably positioned relative to the inner collar of the first component and so that the conduit of the graft element provides fluid communication between (i) the region beyond the inner collar, and (ii) the region beyond the hollow body of the first component.

In another form of the invention, there is provided a delivery instrument for delivering a connector for joining a first hollow structure to the side wall of a second hollow structure, the delivery instrument comprising:
a hollow column;
at least one traction arm pivotally mounted to the hollow column so as to selectively radially project a toe of the traction arm;
a rod movably mounted to the hollow column and having a clamp at the distal end thereof, the rod being adapted to selectively engage the at least one traction arm so as to cause the at least one traction arm to radially project the toe of the at least one traction arm; and at least one collar actuator slidably mounted to the hollow column.

In another form of the invention, there is provided a system for joining a first hollow structure to the side wall of a second hollow structure, the system comprising:

a connector comprising:
  a first component comprising:
    an inner collar for disposition within the interior of the second hollow structure, the inner collar having a toroidal configuration characterized by an outer perimeter and an inner perimeter, with the inner collar being flexible;
    a hollow body connected to the inner collar and upstanding therefrom, the hollow body of the inner collar being aligned with the inner perimeter of the inner collar; and
    a graft element mounted to the inner collar and forming a conduit extending through the hollow body and the inner perimeter of the inner collar, the graft being formed out of a fluid-retaining material;
  a second component for disposition outside the second hollow structure, the second component comprising an outer collar and a hollow body connected to the outer collar, the outer collar having a toroidal configuration characterized by an outer perimeter and an inner perimeter, with the hollow body of the outer collar being aligned with the inner perimeter of the outer collar;
  the hollow body of the second component being sized for coaxial disposition over the hollow body of the first component so that the outer collar of the second component can be adjustably positioned relative to the inner collar of the first component and so that the conduit of the graft element provides fluid communication between (i) the region beyond the inner collar, and (ii) the region beyond the hollow body of the first component; and
a delivery instrument for delivering the connector to the second hollow structure, the delivery instrument comprising:
  a hollow column;
  at least one traction arm pivotally mounted to the distal end of the hollow column so as to selectively radially project a toe of the traction arm;
  a rod movably mounted to the hollow column and having a clamp at the distal end thereof, the rod being adapted to selectively engage the at least one traction arm so as to cause the at least one traction arm to radially project the toe of the at least one traction arm; and
  at least one collar actuator slidably mounted to the hollow column;
the connector being mounted to the delivery tool such that the hollow body of the first component is mounted coaxially on the hollow column of the delivery instrument, and the at least one collar actuator is aligned with the hollow body of the second component.

In another form of the invention, there is provided a method for joining a first hollow structure to the side wall of a second hollow structure, the method comprising:

providing a connector having (i) a first component comprising an inner collar and a hollow graft element mounted to the inner collar and extending therefrom, and (ii) a second component comprising an outer collar;

forming an opening in the side wall of the second hollow structure;

positioning the inner collar of the first component within the interior of the second hollow structure, with the graft element extending through the side wall of the second hollow structure; and advancing the outer collar of the second component toward the inner collar of the first component so as to clamp the side wall of the second hollow structure therebetween.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention comprises a novel method and apparatus for effecting the distal anastomosis in an aortic valve bypass procedure. More particularly, the present invention comprises the provision and use of a novel locking collar connector to effect the distal anastomosis in an aortic valve bypass procedure. This novel locking collar connector allows the distal anastomosis to be effected quickly and safely, while requiring significantly less access to the anastomosis site and without requiring suturing to the descending aorta. Significantly, hemostasis is effectively maintained at substantially all times, so that the distal anastomosis can be carried out while the heart is beating.

Locking Collar Connector

Figure 1:
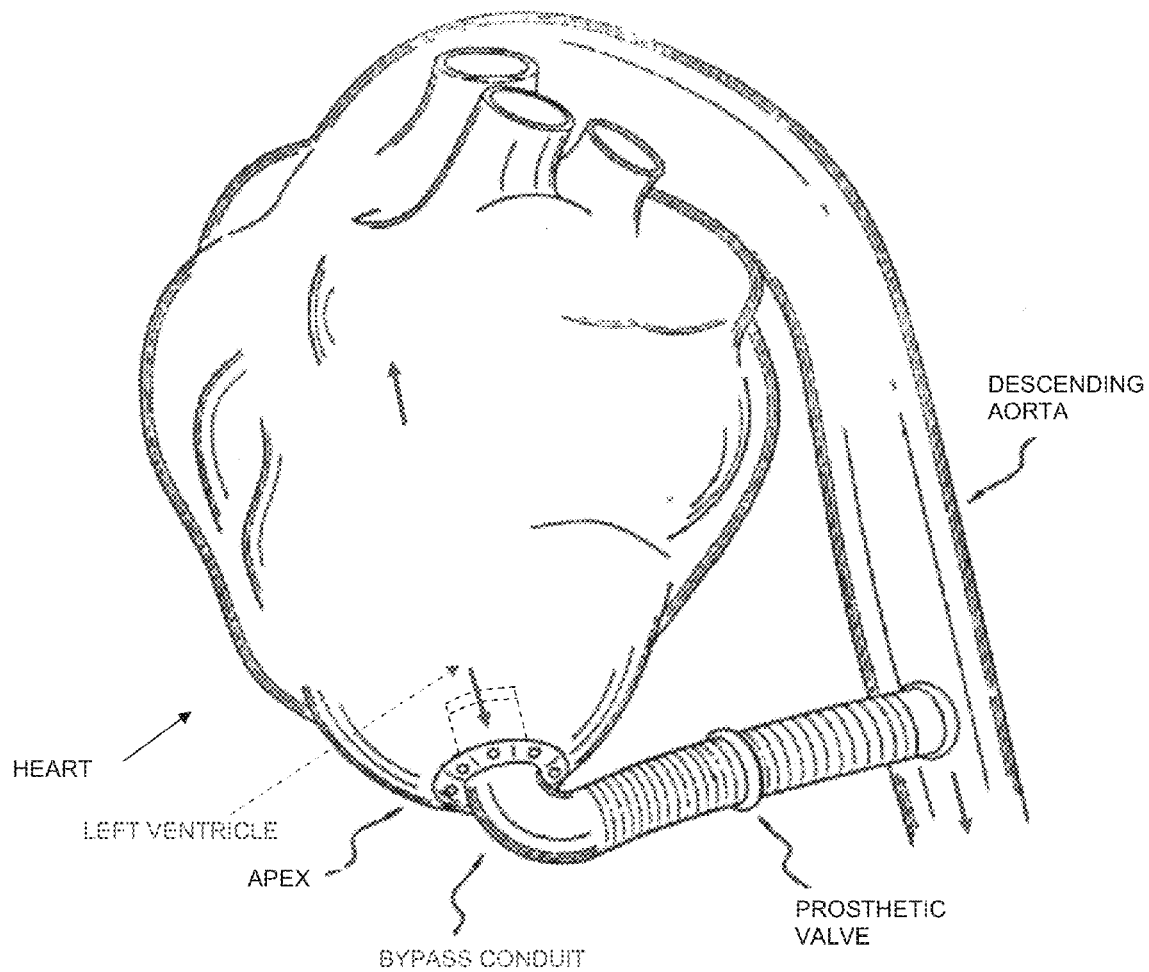
FIG. 1 is a schematic view showing an aortic valve bypass.
Figure 2:
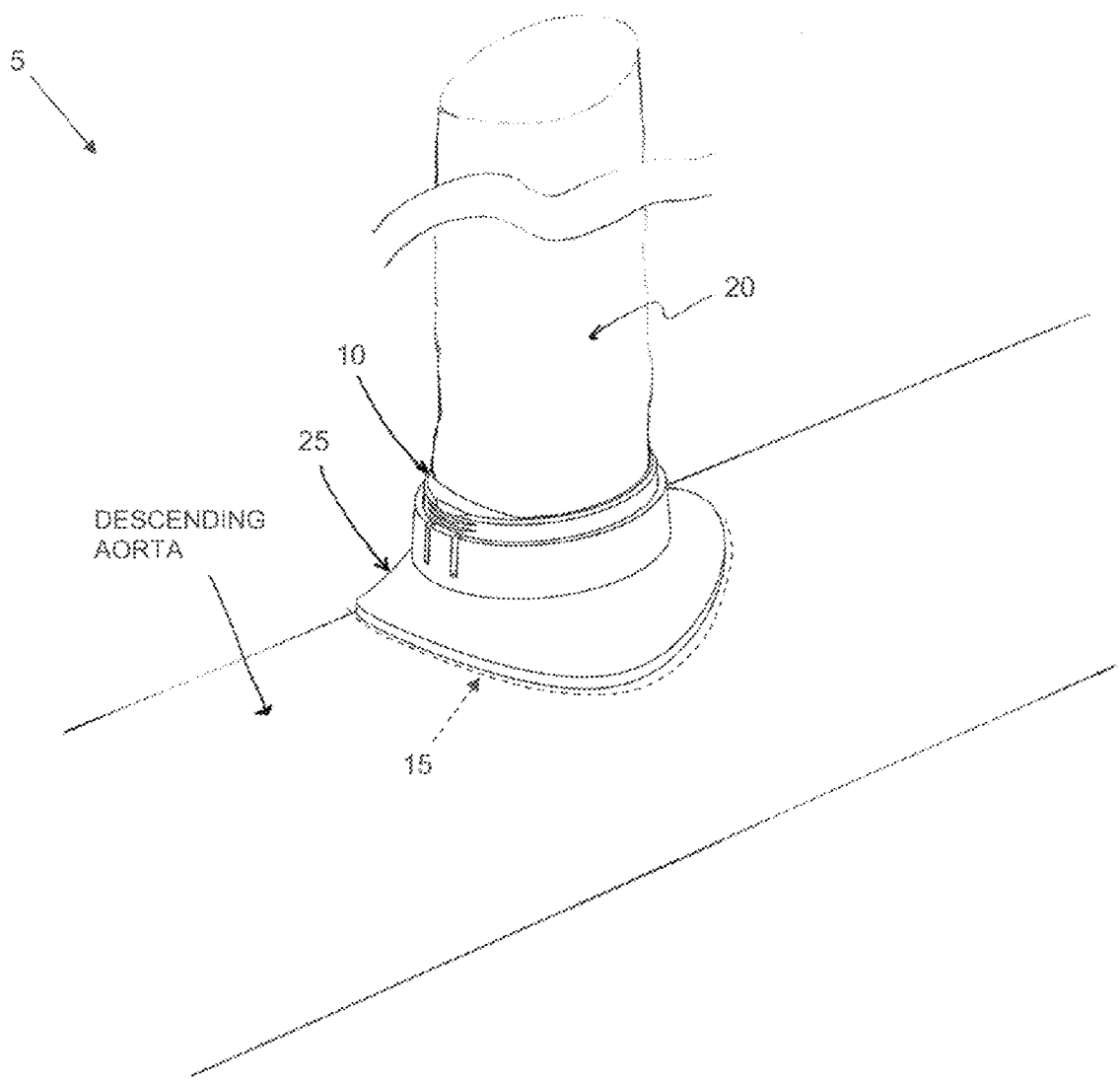
FIG. 2 is a schematic view showing a novel locking collar connector formed in accordance with the present invention and being used to form a distal anastomosis.
Figure 5:
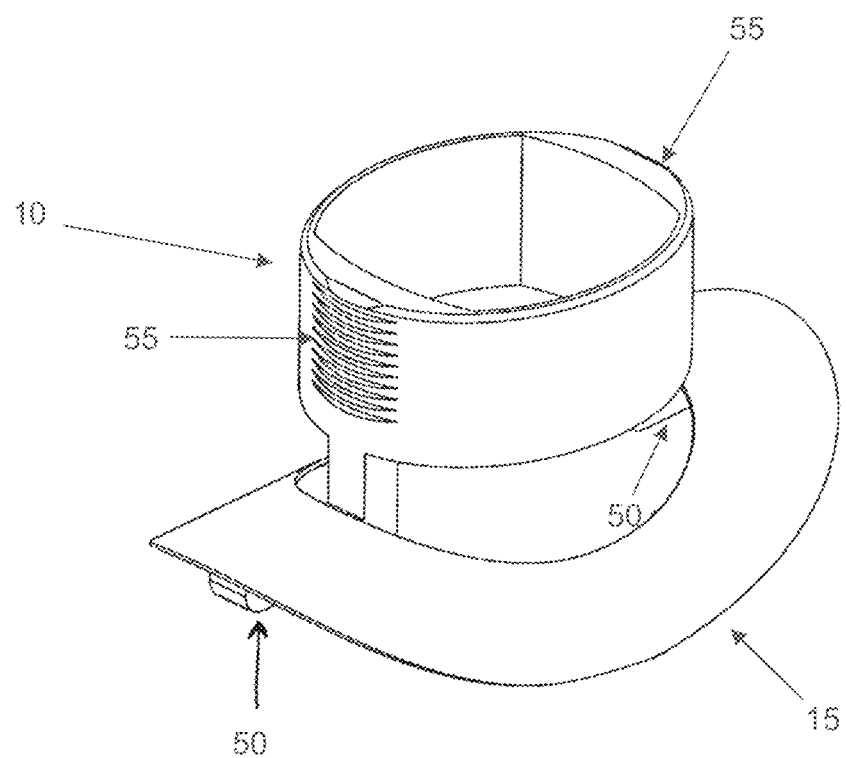
Figure 6:
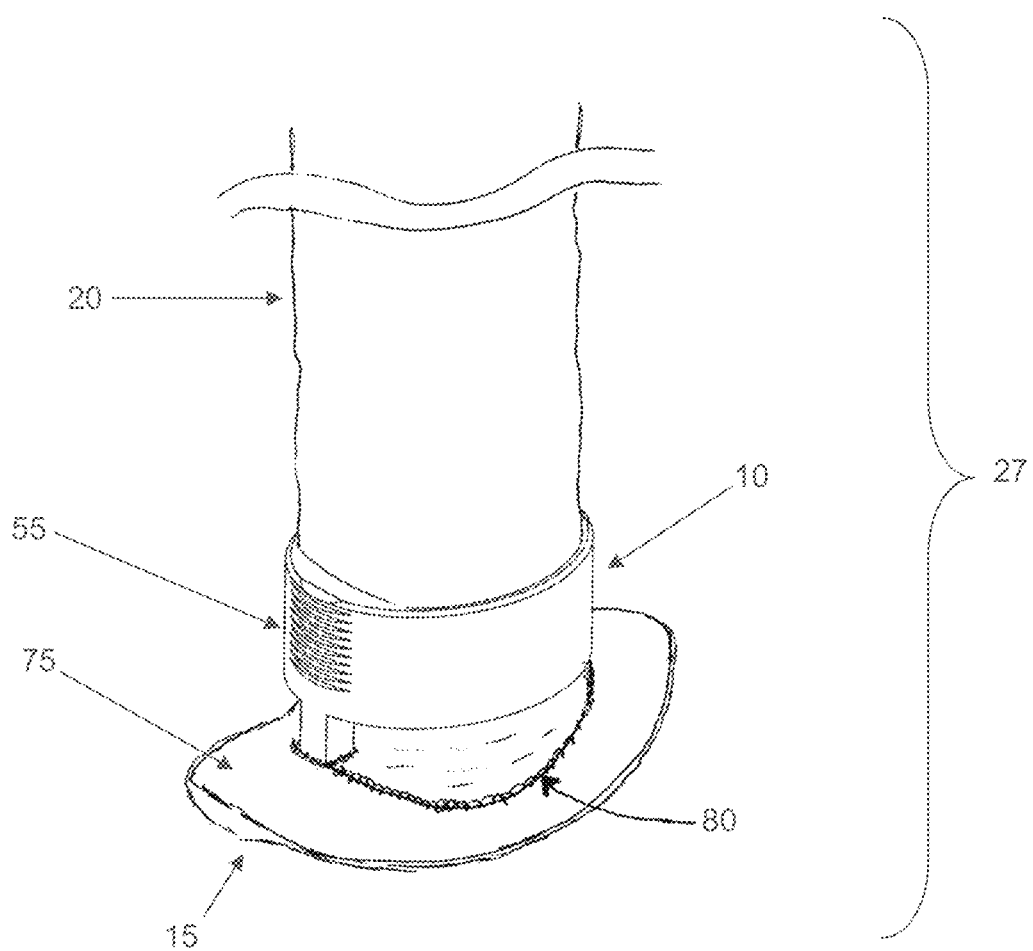
Figure 7:
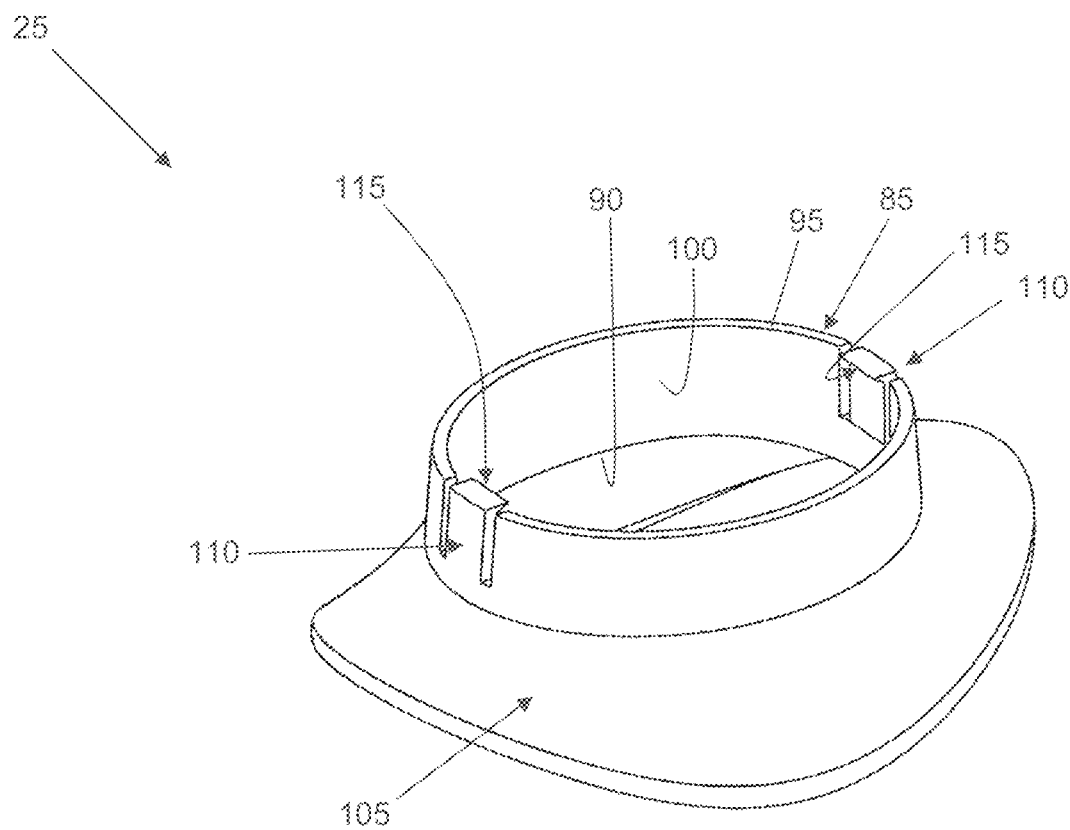

Looking now at FIGS. 2-7, there is shown a novel locking collar connector 5 which comprises one preferred form of the present invention. Locking collar connector 5 generally comprises a ratchet bracket 10 (FIGS. 2, 3, 5 and 6), an inner collar 15 (FIGS. 2, 4, 5 and 6), a graft conduit 20 (FIGS. 2 and 6), and an outer collar 25 (FIGS. 2 and 7). In one preferred form of the present invention, and as will hereinafter be discussed in further detail, ratchet bracket 10, inner collar 15, and graft conduit 20 are assembled into a single integral assembly 27 (FIG. 6) during manufacture, and outer collar 25 (FIG. 7) is joined to this single integral assembly 27 during use (FIG. 2).

Figure 3:
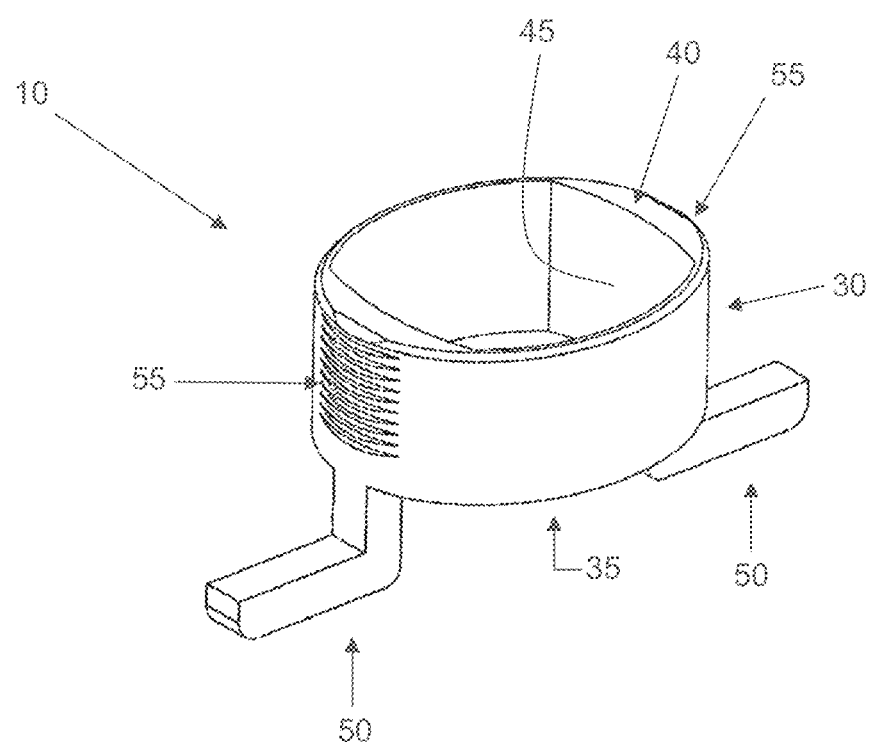
FIGS. 3-7 are schematic views showing various components of the locking collar connector of FIG. 2.
Figure 4:
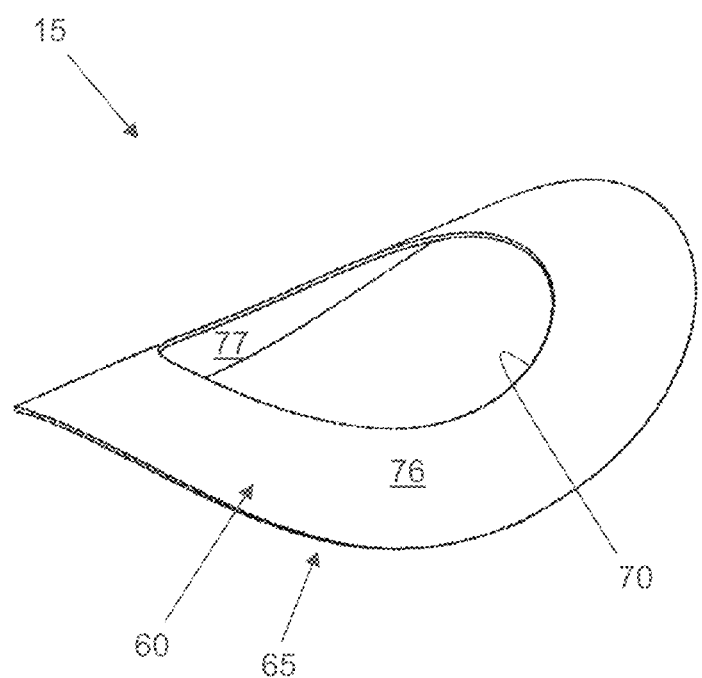

Ratchet bracket 10 is shown in greater detail in FIG. 3. More particularly, ratchet bracket 10 generally comprises a hollow ovoid body 30 having a distal end 35, a proximal end 40, and a lumen 45 extending therebetween. A pair of L-shaped support arms 50 extend distally, and radially outwardly, from distal end 35 of hollow ovoid body 30. Ratchet teeth 55 are provided on the exterior surface of hollow ovoid body 30. Preferably two sets of ratchet teeth 55 are provided on the exterior surface of hollow ovoid body 30, with the two sets of ratchet teeth being disposed in diametrically-opposed disposition, in the manner shown in FIG. 3. As will hereinafter be discussed, graft conduit 20 extends through lumen 45 of hollow ovoid body 30 (FIG. 6), L-shaped support arms 50 are configured to support inner collar 15 adjacent to the distal end of hollow ovoid body 30 (FIGS. 5 and 6), and the two sets of ratchet teeth 55 are configured to be engaged by corresponding elements of outer collar 25 (FIG. 2).

Inner collar 15 (FIGS. 2 and 4-6) comprises a generally ovoid body 60 having an ovoid outer perimeter 65 and an ovoid central hole 70. Inner collar 15 is preferably constructed from a flat sheet of 0.009" thick Nitinol, which is heat-treated while constrained onto the outer diameter of a suitable heat-treat mandrel (about 1.5 inches in diameter) so as to form a resilient saddle-like structure. Alternatively, inner collar 15 can be formed out of other suitable materials. As noted above, and as will hereinafter be discussed, inner collar 15 is intended to be mounted to L-shaped support arms 50 of hollow ovoid body 30 (FIGS. 5 and 6). Furthermore, and as will hereinafter be discussed, inner collar 15 is provided with a spring configuration (e.g., because of its Nitinol construction) which, when inner collar 15 is deployed within the interior of the descending aorta, can exert a substantial sealing force against the inner wall of the descending aorta.

Graft conduit 20 (FIGS. 2 and 6) comprises a generally tubular structure which is preferably constructed out of woven polyester graft (e.g., Vascutek GelWeave™). Other graft materials, including Gore-Tex® fabric or Vascutek Triplex™ material, can also be utilized to form graft conduit 20. As noted above, and as will hereinafter be discussed, graft conduit 20 is configured to extend through lumen 45 of hollow ovoid body 30 (FIG. 6).

As noted above, ratchet bracket 10, inner collar 15 and graft conduit 20 are intended to be assembled into a single integral assembly 27 (FIG. 6) during manufacture, and outer collar 25 is intended to be joined to this integral assembly during use (FIG. 2). More particularly, inner collar 15 is preferably attached to L-shaped support arms 50 of ratchet bracket 10 by molding the ratchet bracket about inner collar 15 so that the inner collar resides on the L-shaped support arms of the ratchet bracket (FIG. 5). Woven graft (e.g., Vascutek GelWeave™) 75 (FIG. 6) is then sewn onto inner collar 15 so as to envelop both sides of the inner collar 15 (i.e., so as to envelop both of the oval faces 76, 77), preferably by stitching the woven graft on both the inner and outer diameters of inner collar 15. Finally, the distal end of graft conduit 20 is sewn (e.g., at a fluid-tight seam 80) to the woven graft 75 covering inner collar 15 (FIG. 6). Fluid-tight seam 80 is preferably on the inner edge of the Nitinol oval, as shown in FIG. 6. Thus, the distal end of the lumen of graft conduit 20 opens on the ovoid central hole 70 of inner collar 15, with inner collar 15 providing a resilient ovoid flange at the distal end of graft conduit 20 (see FIG. 6).

Significantly, with this construction, ratchet bracket 10 remains primarily outside of graft conduit 20 and is not covered with graft material; only the two L-shaped support arms 50 (molded onto the Nitinol oval of inner collar 15) are enclosed in graft material. The two resulting penetrations through the graft layer (i.e., at the locations where the distal end of graft conduit engages the two L-shaped support arms 50) are sutured tightly in order to eliminate potential leak paths.

Outer collar 25 (FIGS. 2 and 7) comprises a hollow ovoid body 85 having a distal end 90, a proximal end 95, and lumen 100 extending therebetween. A flange 105 is mounted to distal end 90 of hollow ovoid body 85. A pair of ratchet arms 110, including ratchet teeth 115 thereon, are spring mounted to hollow ovoid body 85. As will hereinafter be discussed, hollow ovoid body 85 of outer collar 25 is intended to be slid over hollow ovoid body 30 of ratchet bracket 10 so that flange 105 of outer collar 25 opposes inner collar 15, with ratchet teeth 115 of outer collar 25 engaging ratchet teeth 55 of ratchet bracket 10. Outer collar 25 is preferably molded out of a medical grade acetal. Other materials suitable for permanent implant, such as silicone or polypropylene, can also be used.

In use, and as will hereinafter be discussed, an opening is made in the side wall of the descending aorta; the single integral assembly 27 (FIG. 6) of ratchet bracket 10, inner collar 15 and graft conduit 20 is maneuvered so that inner collar 15 is positioned within the interior of the descending aorta while hollow ovoid body 30 and graft conduit 20 extend out the side wall of the descending aorta; and then hollow ovoid body 85 of outer collar 25 is slid down over graft conduit 20 and hollow ovoid body 30 of ratchet bracket 10 until flange 105 of outer collar 25 engages the outer wall of the descending aorta and ratchet teeth 115 of outer collar 25 engage ratchet teeth 55 of ratchet bracket 10, with the side wall of the descending aorta being securely clamped between inner collar 15 and flange 105 of outer collar 25, and with graft conduit 20 in fluid communication with the interior of the descending aorta. In this way, the distal anastomosis can be provided for an aortic valve bypass procedure. Thereafter, graft conduit 20 can be connected, in ways well known in the art, to the left ventricle of the heart as part of an aortic valve bypass procedure.

It will be appreciated that, with this construction, ratchet bracket 10 is instrumental in locking outer collar 25 down onto the outer surface of the descending aorta while simultaneously sandwiching the aortic wall between inner collar 15 and flange 105 of outer collar 25 (FIG. 2). In this respect it will also be appreciated that outer collar 25 has two diametrically-opposed ratchet teeth 115 (FIG. 7), while ratchet bracket 10 has two corresponding diametrically-opposed sets of ratchet teeth 55, with the two diametrically-opposed sets of ratchet teeth 55 being aligned with each end of the inner collar oval's major axis (FIG. 5). With this arrangement, each end of outer collar 25 can be locked into a number of positions relative to ratchet bracket 10 (and hence relative to inner collar 15), thereby accommodating for variable aortic wall thicknesses. In this respect it will also be appreciated that the general oval shape of hollow ovoid body 85 of outer collar 25 and hollow ovoid body 30 of ratchet bracket 10 serves to automatically establish and maintain alignment between the mating ratchet teeth 55, 115 of the ratchet bracket and the outer collar. In other words, relative rotation between the outer collar and ratchet bracket is effectively prevented.

It will also be appreciated that, on account of the foregoing construction, locked collar connector 5 presents only graft material to the lumen of the anastomosis site.

Delivery Instrument

A novel delivery instrument 200 (FIGS. 8-12) is provided to enable the physician to easily install and deploy locked collar connector 5 through a small thoracotomy into a slit in the descending aorta, whereby to form the desired distal anastomosis for the aortic valve bypass.

Looking now at FIGS. 8-12, delivery instrument 200 generally comprises a hollow ovoid column 205 (FIG. 9) having a pair of traction arms 210 movably mounted to the distal end thereof. More particularly, each of the traction arms 210 is pivotally mounted to hollow ovoid column 205 via a pivot pin 220, whereby a toe 225 thereof may be moved radially inwardly or outwardly relative to the longitudinal axis 230 of hollow ovoid column 205. A garter spring 235 is provided so as to urge toes 225 of traction arms 210 radially inwardly. A pair of handles 240 (FIG. 8) are attached to hollow ovoid column 205.

Figure 15:
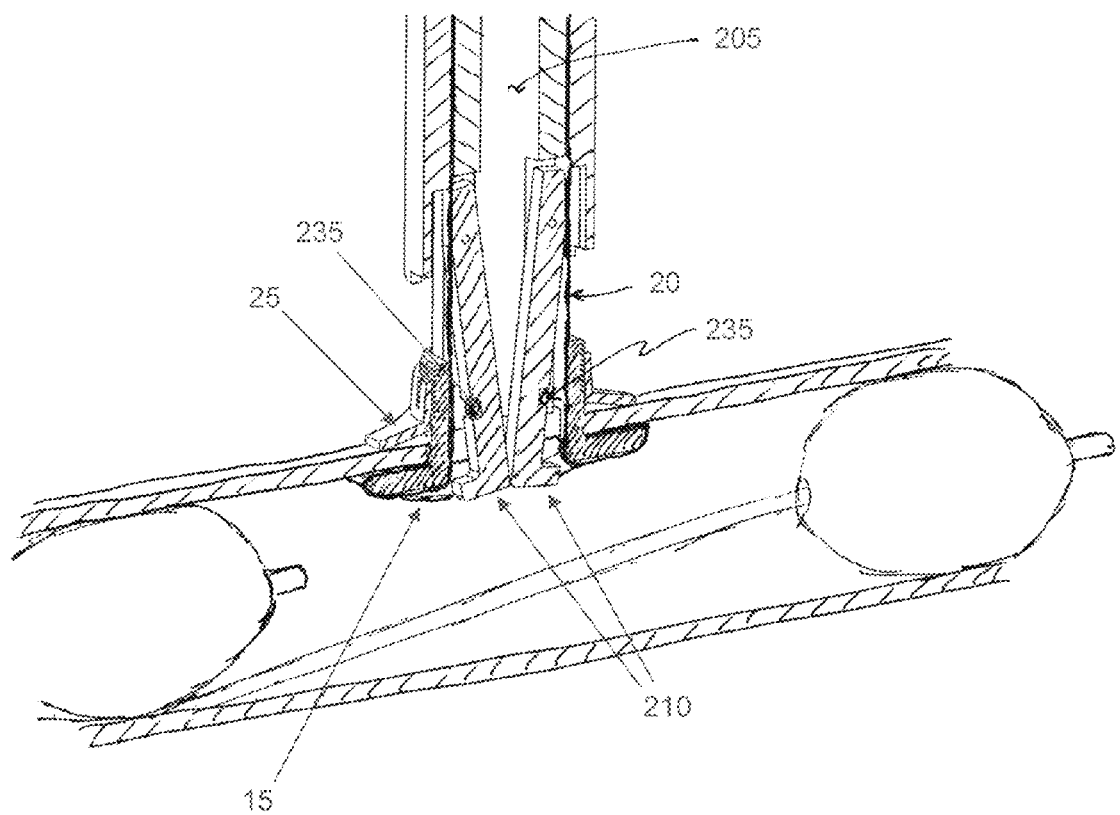

Still looking at FIGS. 8-12, a clothespin rod 245, having a bifurcated clothespin clamp 250 at its distal end, is movably mounted within hollow ovoid column 205. As will hereinafter be discussed, clothespin clamp 250 may be used to keep inner collar 15 of locking collar connector 5 folded along its long axis. When clothespin rod 245 is in its extended position (FIG. 9), clothespin rod 245 forces traction arms 210 apart, whereby to radially project toes 225, in the manner shown in FIG. 9. In this way, and as will hereinafter be discussed, toes 225 can be used to support the undersides of L-shaped support arms 50 of inner collar 15, whereby to grasp inner collar 15 to delivery instrument 200. When clothespin rod 245 is in its retracted position (FIG. 15), garter spring 235 urges toes 225 radially inwardly, in the manner shown in FIG. 15. In this way, and as will hereinafter be discussed, toes 225 can be withdrawn from the undersides of L-shaped support arms 50 of inner collar 15, whereby to release inner collar 15 from delivery instrument 200.

Still looking at FIGS. 8-12, a pair of collar actuators 255 are movably disposed about the exterior of hollow column 205. More particularly, collar actuators 255 include a pair of slots 260 through which handles 240 project. By gripping handles 240 and pressing on the proximal ends of collar actuators 255, the distal ends of collar actuators 255 can be moved distally, whereby to force outer collar 25 distally, as will hereinafter be discussed. Collar actuators 255 together have an ovoid configuration.

To install locking collar connector 5 onto delivery instrument 200, collar actuators 255 are moved proximally on hollow ovoid column 205, and clothespin rod 245 is moved proximally within hollow ovoid column 205 so that toes 225 are retracted inboard. Next, outer collar 25 of locking collar connector 5 is slid onto the distal end of hollow ovoid column 25. Then the single integral assembly 27 of ratchet bracket 10, inner collar 15 and graft conduit 20 is slid onto the distal end of hollow ovoid column 205. Next, inner collar 15 is folded along the major axis of the oval. Then clothespin rod 245 is moved distally so that toes 225 project radially outward so as to support the underside of ratchet bracket 10 and so that clothespin clamp 250 holds portions of the Nitinol oval of the inner collar 15 in close proximity across the oval's minor axis. See FIGS. 8-12. Thus, the single integral assembly 27 of ratchet bracket 10, inner collar 15 and graft conduit 20 is securely held in place on the distal end of delivery instrument 200, with graft conduit 20 trapped in the annular gap between hollow ovoid column 205 and collar actuators 255, and with outer collar 25 of locking collar connector 5 disposed on hollow ovoid column 205 proximal to the aforementioned single integral assembly 27 (of ratchet bracket 10, inner collar 15 and graft conduit 20) and distal to collar actuators 255.

Note that a portion of graft conduit 20 is folded under, and is also held by, clothespin clamp 250. See FIGS. 10 and 13.

When locking collar connector 5 is to be deployed off the distal end of delivery instrument 200, collar actuators 255 are advanced distally while hollow ovoid column 205 is held stationary (e.g., via handles 240). This causes outer collar 25 of locking collar connector 5 to move distally, with flange 205 of outer collar 205 moving toward inner collar 15 so as to clamp vascular tissue therebetween, and with ratchet teeth 115 of outer collar 25 engaging ratchet teeth 55 of ratchet bracket 10 so as to lock the two members in position relative to one another, and with graft conduit 20 in fluid communication with the desired blood flow. With locking collar connector 5 in position, clothespin rod 245 is retracted proximally, releasing inner collar 15 from clothespin clamp 250 (whereupon inner collar 15 springs back to its unfolded condition) and allowing toes 225 to retract inwardly, whereby to free delivery instrument 200 from locking collar connector 5. Delivery instrument 200 may thereupon be withdrawn from the surgical site, leaving locking collar connector 5 in position. In this way, the distal anastomosis can be provided for an aortic valve bypass procedure. Thereafter, graft conduit 20 can be connected, in ways well known in the art, to the left ventricle of the heart as part of an aortic valve bypass procedure.

Installation Method

The preferred method for installing locking collar connector 5 into the descending aorta using delivery instrument 200 is detailed in the steps below.

1. Access to the descending aorta is created through a small thoracotomy, a thoracoscopy, or other minimally invasive opening in the thoracic cavity.

2. Two balloon catheters (Cook Coda® G36042, for example) are fed up from the groin through one or both femoral arteries. A first balloon ("the proximal balloon") is inflated above the anastomosis site (proximal to the heart), and the second balloon is inflated distal to the anastomosis site ("the distal balloon"). See FIG. 13. Blood flow through the aorta is effectively blocked by the two inflated balloons.

Figure 13:
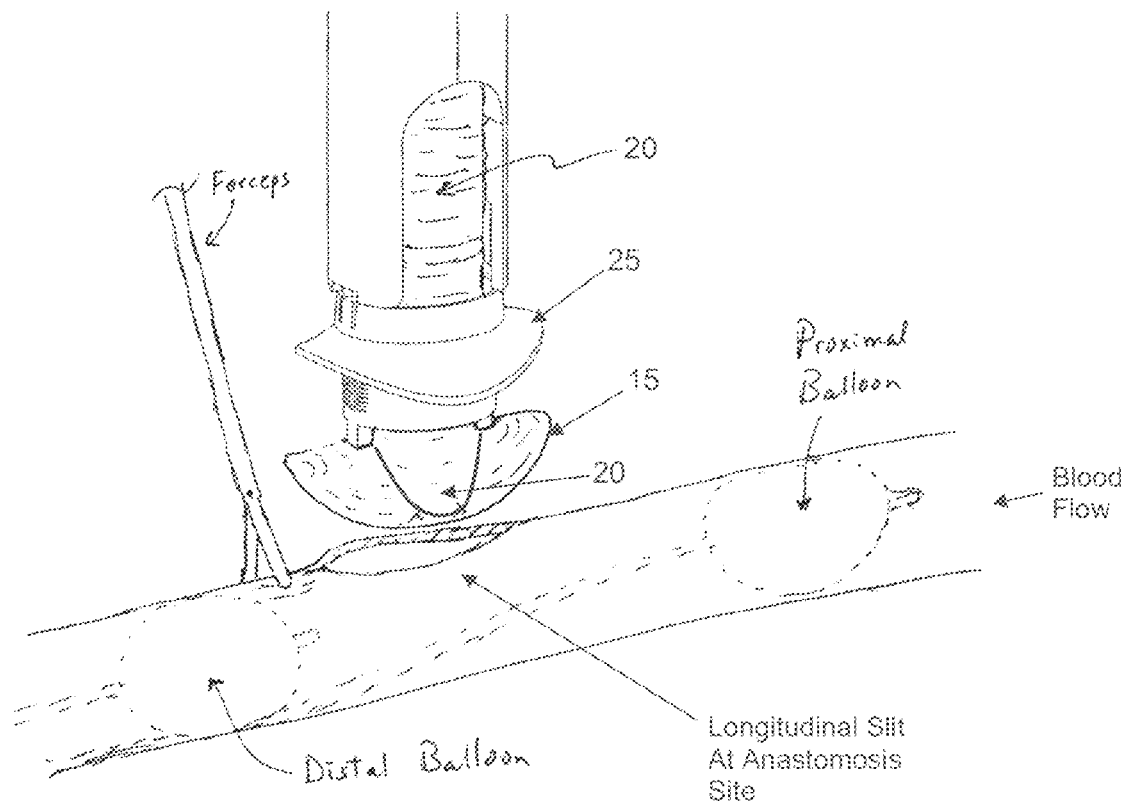
FIGS. 13-15 are schematic views showing a distal anastomosis being formed with the locking collar connector and delivery instrument of FIG. 8.

3. The physician cuts a longitudinal slit at the anastomosis site (FIG. 13).

4. Delivery instrument 200, with locking collar connector 5 carried thereon, is advanced through the thoracotomy to the anastomosis site. The delivery instrument is rotated so that the major axis of inner collar 15 of locking collar connector 5 is aligned with the aortic slit (FIG. 13). Then inner collar 15 is inserted into the interior of the descending aorta via the aortic slit. In this respect it will be appreciated that insertion of the inner collar through the aortic slit and into the lumen of the descending aorta can be aided by "picking up" the descending aorta adjacent to the slit with a suitable pair of forceps (FIG. 13), and the folded inner collar presents a narrow profile that can be fed one end at a time into the aortic slit. The process is repeated at the other end of the aortic slit until inner collar 15 is fully positioned within the lumen of the descending aorta.

Figure 8:
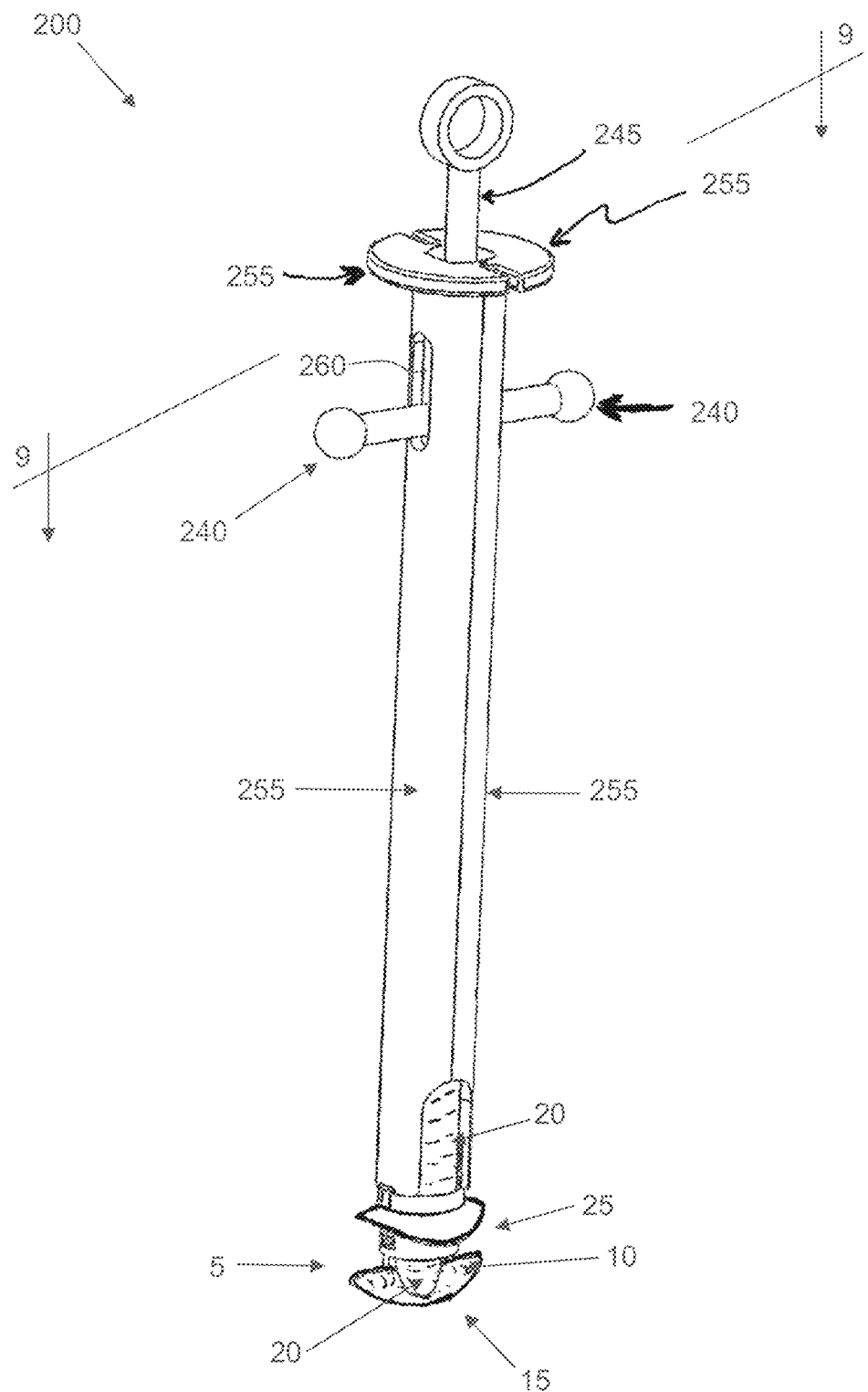
FIG. 8 is a schematic view showing the locking collar connector of FIG. 2 mounted to a novel delivery instrument also formed in accordance with the present invention.
Figure 9:
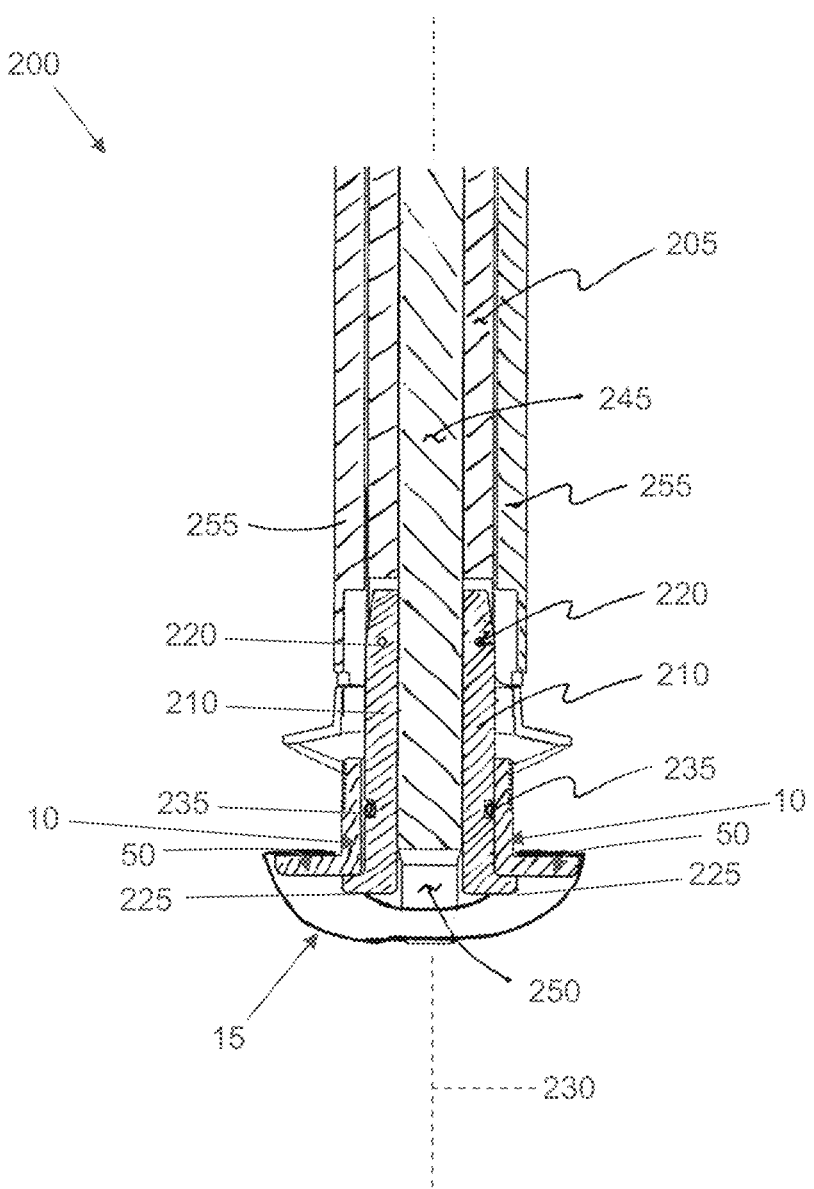
FIGS. 9-12 are schematic views showing various aspects of the delivery instrument and locking collar connector shown in FIG. 8, with FIG. 9 being a sectional view taken through line 9-9 of FIG. 8; with FIG. 10 being an enlarged end view of the distal end of the delivery instrument and locking collar connector of FIG. 8; with FIG. 11 being an end view like that of FIG. 10, but with the graft material removed for clarity of illustration; with FIG. 12 being an enlarged side view of the distal end of the delivery instrument and locking collar connector, but with the graft material removed for clarity of illustration.
Figure 10:
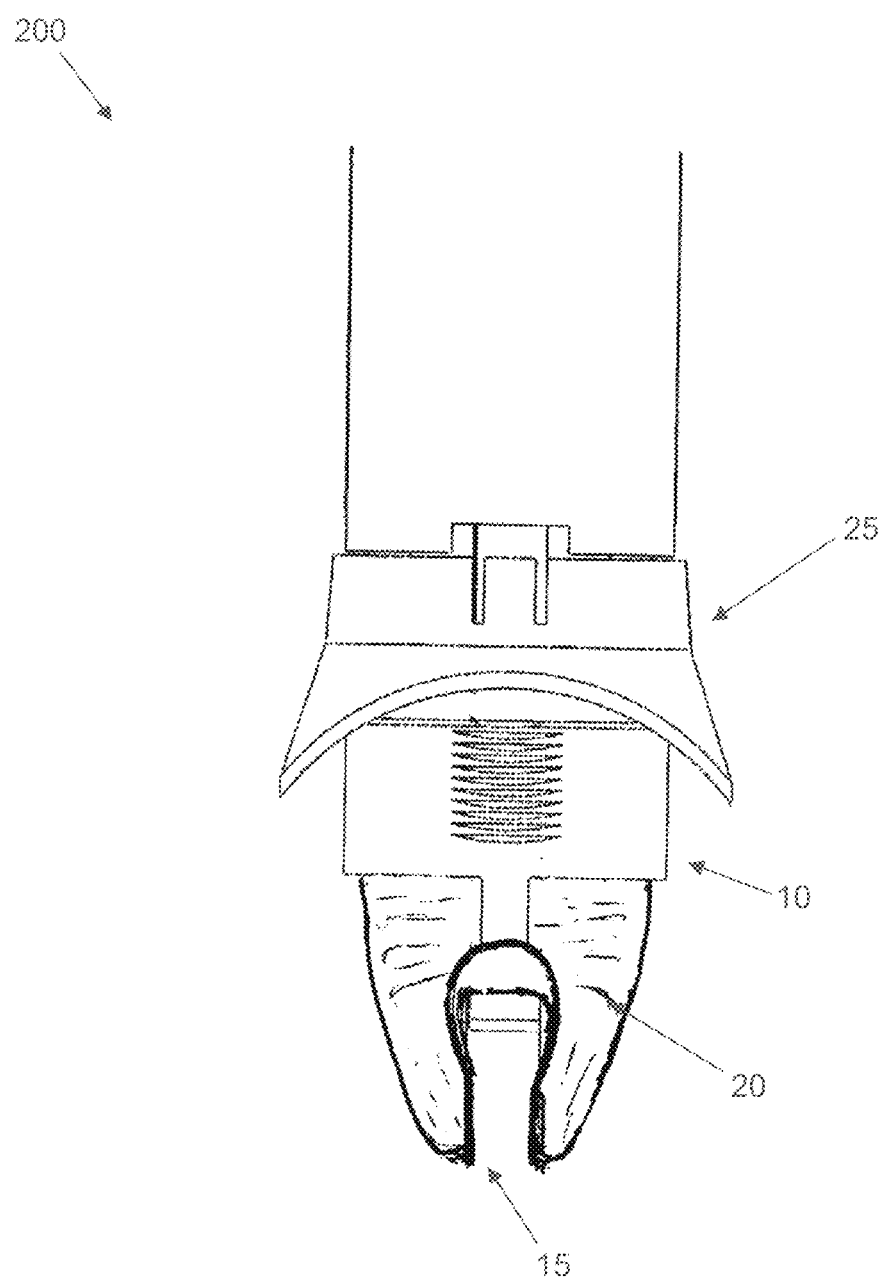
Figure 11:
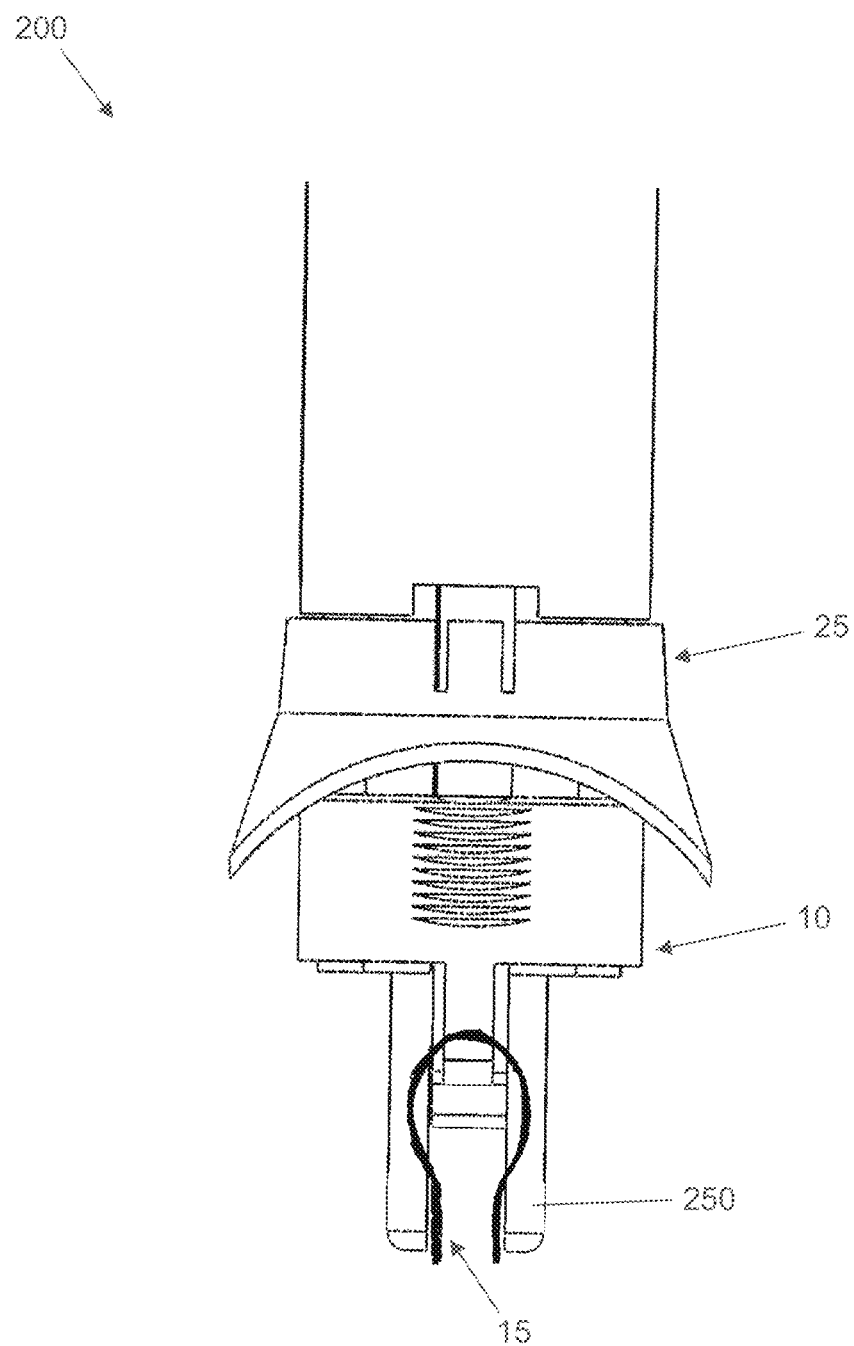
Figure 12:
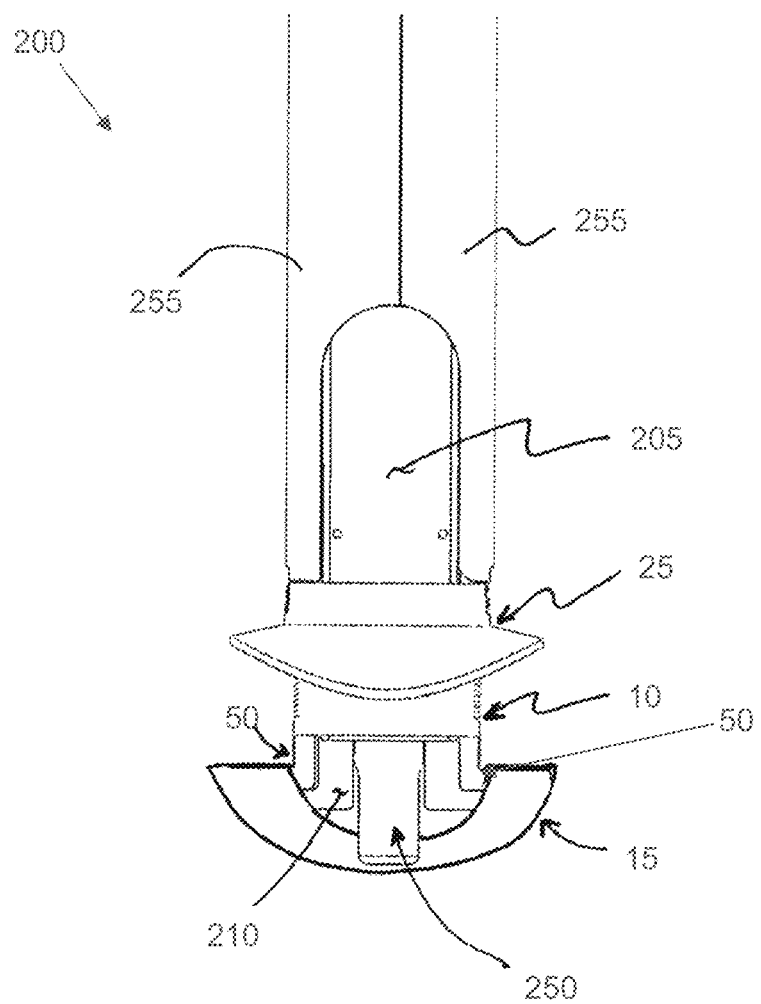
Figure 14:
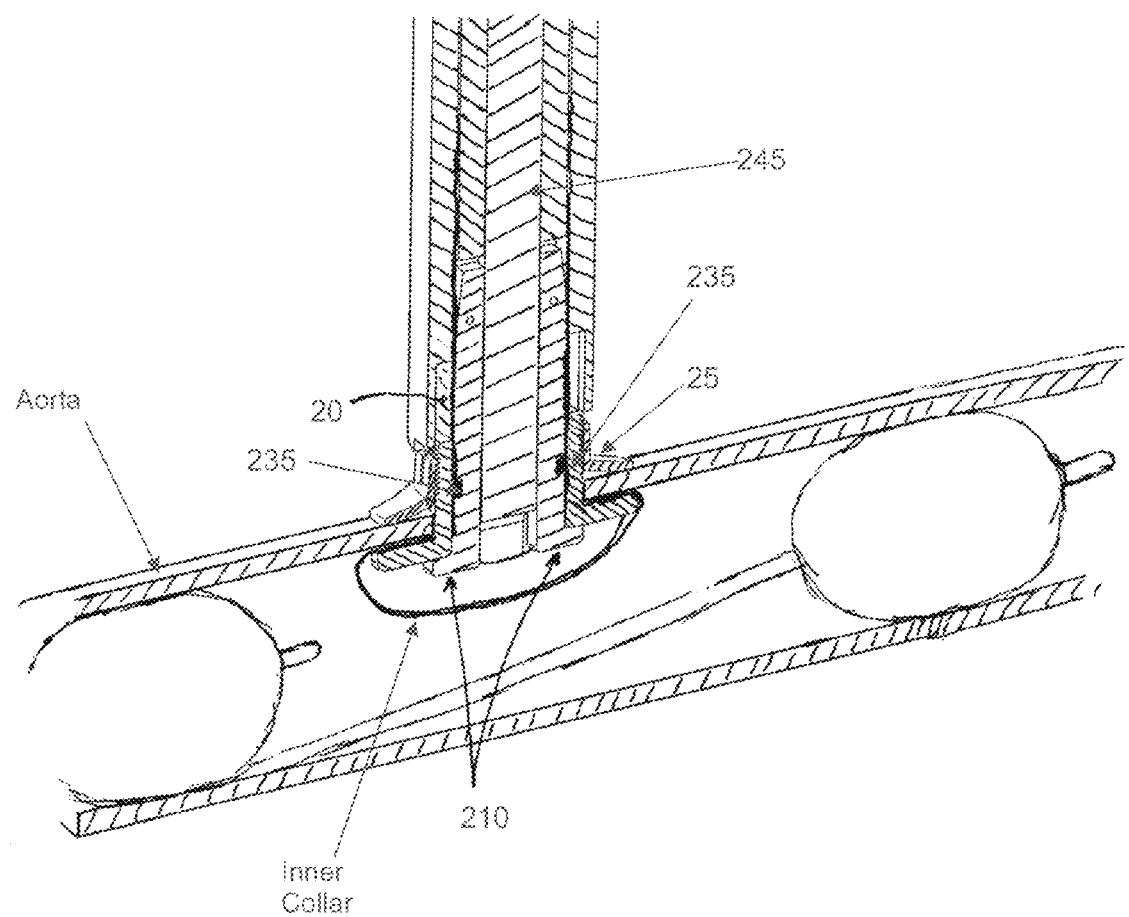

5. Once inner collar 15 of locking collar connector 5 is within the lumen of the descending aorta and substantially centered on the aortic slit, the physician applies traction to the inner collar via handles 240 (FIG. 8). As noted above, the handles are rigidly connected to hollow ovoid column 205, which contains the pivot axes for traction arms 210. The traction arms are in contact with the ratchet bracket's L-shaped support arms 50 through a layer of graft. With traction applied to inner collar 15 using the handles as described above, the physician advances outer collar 25 down onto ratchet bracket 10 (FIG. 14). To this end, delivery instrument 200 has a pair of collar actuators 255 (FIG. 9) that may be moved independently of one another. The physician is able to push on either, or both, collar actuators as required so as to set outer collar 25. This provides tactile feedback to the physician and enables him to properly compress each end of the outer collar onto the ratchet bracket. The aortic wall is thus securely clamped between outer collar 25 and the portion of the inner collar 15 near the major axis of the Nitinol oval of the inner collar. As this occurs, ratchet teeth 115 of outer collar 25 and ratchet teeth 55 of ratchet bracket 10 engage with each other so as to prevent the inner collar and the outer collar from separating. See FIG. 14.

6. The physician retracts clothespin rod 245, pulling clothespin clamp 250 off the folded inner collar 15. As a result, the inner collar springs outward until the inner wall of the descending aorta is encountered. There is sufficient spring force in the inner collar to create at least line-to-line contact along the entire inner circumference of the aortic slit, thereby establishing hemostasis. As clothespin rod 245 is further retracted, the two traction arms 210 pivot towards each other, moving toes 225 inboard and thereby releasing support arms 50 from the delivery instrument. This action is preferably aided by the provision of garter spring 235. See FIG. 15.

7. Collar actuators 255 and hollow ovoid column 205 are withdrawn. The graft conduit slips out from the annular gap between the hollow ovoid column and the collar actuators.

8. Means to block the neck of graft conduit 20, and maintain hemostasis, are provided. By way of example but not limitation, a cross-clamp on the graft conduit is one such simple approach. After the graft conduit has been blocked and hemostasis is ensured, the distal balloon is deflated and withdrawn. Then the proximal balloon is deflated and withdrawn, leaving locking collar connector 5 deployed within the descending aorta.

9. At this point, the distal anastomosis for the aortic valve bypass procedure is complete. Graft conduit 20 can thereafter be connected, in ways well known in the art, to the left ventricle of the heart as part of an aortic valve bypass procedure.

Alternative Constructions for the Locking Collar Connector

Figure 16:
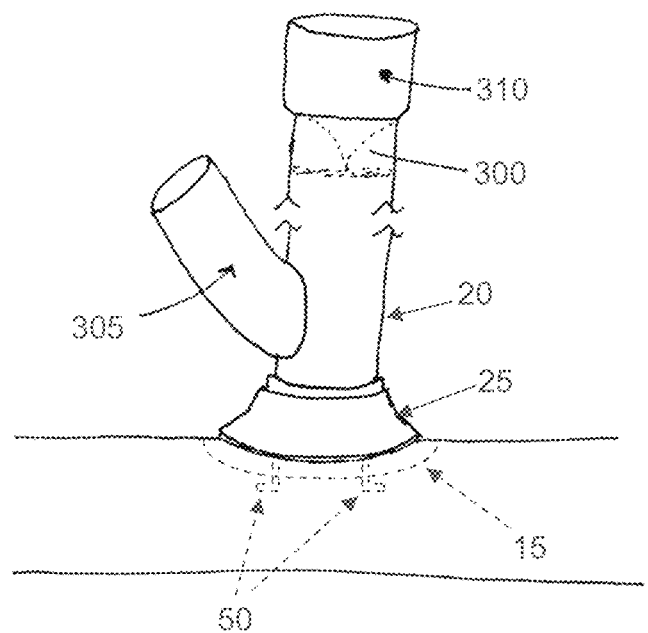
FIG. 16 is a schematic view showing an alternative form of locking collar connector formed in accordance with the present invention.

An alternative embodiment of the locking collar connector is shown schematically in FIG. 16, and includes:

1. A prosthetic valve 300 is pre-installed in the proximal end of graft conduit 20.

2. A side branch 305 is provided on graft conduit 20. This construction is useful when a valve is pre-installed in the graft conduit. In this form of the invention, side branch 305 is installed on the delivery instrument (see below), and graft conduit 20 hangs off to the side of the delivery instrument. Side branch 305 is preferably sized to fit in the annular gap between the hollow ovoid column and the collar actuators.

3. A connector 310 is provided for attaching the proximal end of graft conduit 20 to another conduit. This connector may be (i) a male-female slip connector such as is taught in FIG. 15 of U.S. Pat. No. 7,510,561, issued Mar. 31, 2009 to Richard M. Beane et al. for APPARATUS AND METHOD FOR CONNECTING A CONDUIT TO A HOLLOW ORGAN, which patent is hereby incorporated herein by reference, and/or (ii) a snap-together coupling of the sort known in the fluid-coupling art, with self-sealing capability on at least one side of the coupling.

Inner collar 15 may also be constructed out of a stacked set of thin oval steel washers, rather than out of a single Nitinol sheet 0.009" thick. By way of example but not limitation, a set of (4) 0.002" thick stainless steel ovals can be stacked and joined together when the ratchet bracket is over-molded. Acting in tandem, this stack of stainless steel oval sheets can provide suitable flexibility and spring force with a low attendant stress level. Consequently, the risk of a fatigue failure can be significantly reduced.

Variation to the Foregoing Installation Method

Where a side branch 305 is present on graft conduit 20, the side branch can be held within the delivery instrument instead of the graft conduit. Installation then proceeds as outlined above. One advantage of this alternative configuration and approach is that a prosthetic valve 300 can be pre-installed within the graft conduit where a side branch is provided. The graft conduit, with valve, then remains undisturbed throughout the distal anastomosis.

Use of the Present Invention for Other Applications

As disclosed above, the present invention may be used for effecting a distal anastomosis for an aortic valve bypass. However, it should be appreciated that the present invention can also be used for a distal anastomosis for any bypass procedure, or for substantially any joinder of one vessel to another vessel.

Further Modifications

It will be understood that many additional changes in the details, materials, steps and arrangements of parts, which have been herein described and illustrated in order to explain the nature of the invention, may be made by those skilled in the art while remaining within the principles and scope of the present invention.

What is claimed is:

1. A method for joining a first hollow structure to the side wall of a second hollow structure, the method comprising:
   providing a connector having (i) a first component comprising an inner collar and a hollow graft element mounted to the inner collar and extending therefrom, and (ii) a second component comprising an outer collar;
   forming an opening in the side wall of the second hollow structure;
   positioning the inner collar of the first component within the interior of the second hollow structure, with the graft element extending through the side wall of the second hollow structure; and
   advancing the outer collar of the second component toward the inner collar of the first component so as to clamp the side wall of the second hollow structure therebetween;

wherein the inner collar of the first component is flexible, and further wherein positioning the inner collar of the first component within the interior of the second hollow structure comprises folding the inner collar along an axis thereof prior to inserting the inner collar into the second hollow structure, and thereafter restoring the inner collar to its initial configuration after insertion of the inner collar into the second hollow structure;

wherein the first component comprises a resilient structure, and further wherein folding the inner collar along an axis thereof includes restraining the inner collar in a folded configuration with a restraint, and wherein restoring the inner collar to its initial configuration includes releasing the restraint;

wherein the restraint comprises a clothespin clamp; and wherein the clothespin clamp is disposed within the interior of the graft element.

2. A method according to claim 1 further comprising connecting the graft element to the first hollow structure.

3. A method according to claim 1 wherein the inner collar comprises an ovoid structure, and further wherein said axis comprises the long axis of the ovoid structure.

4. A method according to claim 1 wherein the inner collar comprises a neck upstanding from the remainder of the inner collar.

5. A method according to claim 4 wherein the outer collar is configured to be passed over the neck.

6. A method according to claim 1 wherein the inner collar and the outer collar are adjustably connected to one another by a ratchet mechanism.

7. A method according to claim 1 wherein the inner collar comprises a shape memory alloy.

8. A method according to claim 1 wherein the inner collar conforms to the curvature of the inside wall of the second hollow structure.

9. A method according to claim 1 wherein the outer collar conforms to the curvature of the outer wall of the second hollow structure.

10. A method according to claim 1 wherein the inner collar is enveloped with graft material.

11. A method according to claim 1 wherein fluid flow through the second hollow structure is halted prior to forming an opening in the side wall of the second hollow structure.

12. A method according to claim 11 wherein fluid flow is halted by:
  delivering a first balloon within the lumen of the second hollow structure proximal to where the opening is to be formed in the side wall of the second hollow structure;
  inflating the first balloon within the lumen of the second hollow structure;
  delivering a second balloon within the lumen of the second hollow structure distal to where the opening is to be formed in the side wall of the second hollow structure; and
  inflating the second balloon within the lumen of the second hollow structure.

* * * * *